US012736448B2

(12) United States Patent
Shen et al.

(10) Patent No.: US 12,736,448 B2
(45) Date of Patent: Sep. 15, 2026

(54) SET CEMENT MECHANICAL PROPERTIES PARAMETER MEASUREMENT METHOD AND APPARATUS BASED ON IMAGE RECOGNITION TECHNOLOGY

(71) Applicants: China National Petroleum Corporation, Beijing (CN); CNPC Engineering Technology R&D Company Limited, Beijing (CN)

(72) Inventors: Jiyun Shen, Beijing (CN); Hongfei Ji, Beijing (CN); Xueli Guo, Beijing (CN); Jianzhou Jin, Beijing (CN); Yongjin Yu, Beijing (CN); Congfeng Qu, Beijing (CN); Fengzhong Qi, Beijing (CN); Zhao Huang, Beijing (CN); Xiujian Xia, Beijing (CN); Huiting Liu, Beijing (CN); Yongqin Cheng, Beijing (CN); Pengyang Jia, Beijing (CN); Zhengyang Zhao, Beijing (CN)

(73) Assignees: CHINA NATIONAL PETROLEUM CORPORATION, Beijing (CN); CNPC ENGINEERING TECHNOLOGY R&D COMPANY LIMITED, Beijing (CN)

( * ) Notice: Subject to any disclaimer, the term of this patent is extended or adjusted under 35 U.S.C. 154(b) by 329 days.

(21) Appl. No.: 18/572,483

(22) PCT Filed: Oct. 26, 2022

(86) PCT No.: PCT/CN2022/127680
§ 371 (c)(1),
(2) Date: Dec. 20, 2023

(87) PCT Pub. No.: WO2023/216519
PCT Pub. Date: Nov. 16, 2023

(65) Prior Publication Data

US 2024/0288348 A1 Aug. 29, 2024

(30) Foreign Application Priority Data

May 13, 2022 (CN) ......................... 202210524615.9

(51) Int. Cl.
*G01N 3/06* (2006.01)
*G01N 3/08* (2006.01)
*G01N 33/38* (2006.01)

(52) U.S. Cl.
CPC ............... *G01N 3/068* (2013.01); *G01N 3/08* (2013.01); *G01N 33/383* (2013.01);
(Continued)

(58) Field of Classification Search
CPC ........ G01N 3/068; G01N 3/08; G01N 33/383; G01N 2203/0019; G01N 2203/0075;
(Continued)

(56) References Cited

U.S. PATENT DOCUMENTS 11,481,894 B1 * 10/2022 Wang ..................... G01B 11/16
2008/0192987 A1 8/2008 Helgason et al.
(Continued)

FOREIGN PATENT DOCUMENTS

CN 104142268 A 11/2014
CN 108169022 A 6/2018
(Continued)

OTHER PUBLICATIONS

Machine translation of CN-113466066-A (Year: 2021).*
(Continued)

*Primary Examiner* — David J Bolduc
(74) *Attorney, Agent, or Firm* — Volpe Koenig

(57) ABSTRACT

A set cement mechanical property parameter measurement method and apparatus based on image recognition technology. The method includes: acquiring a first image of a set cement specimen; extracting at least one feature point in the
(Continued)

first image; acquiring a second image of the set cement specimen, the second image being an image of the set cement specimen subjected to a compressive load during a compressive test; determining a deformation gradient of the feature point by positions of the same feature point in the first image and the second image; determining a strain tensor by the deformation gradient; and determining a Young's modulus parameter and a Poisson's ratio parameter by the strain tensor. The method can reduce the measurement period of the Young's modulus and Poisson's ratio of the set cement specimens, simplify the corresponding operation process, and reduce the corresponding measurement error.

18 Claims, 5 Drawing Sheets

(52) U.S. Cl.
CPC ................ *G01N 2203/0019* (2013.01); *G01N 2203/0075* (2013.01); *G01N 2203/0098* (2013.01); *G01N 2203/0218* (2013.01); *G01N 2203/0647* (2013.01); *G01N 2203/0682* (2013.01)

(58) Field of Classification Search
CPC .............. G01N 2203/0098; G01N 2203/0218; G01N 2203/0647; G01N 2203/0682; G01N 3/06; G01N 2203/0003; G01N 2203/0676
See application file for complete search history.

(56) References Cited

U.S. PATENT DOCUMENTS

| | | | | |
|---|---|---|---|---|
| 2011/0066390 | A1* | 3/2011 | Macleod | G01N 3/06 702/56 |
| 2011/0254573 | A1* | 10/2011 | Shtakelberg | G01N 33/383 324/693 |
| 2013/0063570 | A1* | 3/2013 | Michopoulos | G01B 11/165 348/47 |
| 2015/0355158 | A1* | 12/2015 | Lander | G01N 33/24 702/2 |
| 2017/0205388 | A1* | 7/2017 | Thomas | G01N 33/383 |
| 2018/0266809 | A1* | 9/2018 | Chen | G01N 3/08 |
| 2019/0368988 | A1* | 12/2019 | Ju | G06T 7/0004 |
| 2020/0064122 | A1* | 2/2020 | Nawrot | G01B 7/16 |
| 2020/0116475 | A1* | 4/2020 | Lessner | G01N 1/38 |
| 2020/0264082 | A1* | 8/2020 | Shao | G06T 7/68 |
| 2020/0333318 | A1* | 10/2020 | Benkley | G16C 60/00 |
| 2021/0207470 | A1* | 7/2021 | Pisklak | G01N 23/20091 |
| 2021/0333181 | A1* | 10/2021 | Zhang | G01N 3/068 |
| 2021/0357555 | A1 | 11/2021 | Liu et al. | |

FOREIGN PATENT DOCUMENTS

| | | | | | |
|---|---|---|---|---|---|
| CN | 108489413 | A | | 9/2018 | |
| CN | 109269893 | A | | 1/2019 | |
| CN | 109559348 | A | | 4/2019 | |
| CN | 109883333 | A | | 6/2019 | |
| CN | 111429394 | A | | 7/2020 | |
| CN | 112052592 | A | | 12/2020 | |
| CN | 112254656 | A | | 1/2021 | |
| CN | 113340732 | A | | 9/2021 | |
| CN | 113466066 | A | * | 10/2021 | G01N 3/32 |
| CN | 113987752 | A | | 1/2022 | |
| EA | 010956 | B1 | | 12/2008 | |
| JP | 2005-207745 | A | | 8/2005 | |
| RU | 2045070 | C1 | | 9/1995 | |
| WO | 2018/007505 | A1 | | 1/2018 | |

OTHER PUBLICATIONS

Yuxing Wu et al., Experimental and finite element modelling evaluation of cement integrity under diametric compression, Journal of Petroleum Science and Engineering, vol. 188, 2020, 106844, ISSN 0920-4105 (Year: 2020).*
Russian Office Action and Search Report issued on Jul. 29, 2024 for Russian Patent Application No. 2023133875/28 (074538).

* cited by examiner

SET CEMENT MECHANICAL PROPERTIES PARAMETER MEASUREMENT METHOD AND APPARATUS BASED ON IMAGE RECOGNITION TECHNOLOGY

FIELD OF THE INVENTION

The present disclosure relates to the technical field of mechanical property parameter measurement, and particularly to a method for measuring parameters of mechanical properties of set cement based on an image recognition technology, an apparatus for measuring parameters of mechanical properties of set cement based on an image recognition technology, an electronic device, and a computer-readable storage medium.

BACKGROUND OF THE INVENTION

The well-cementing cement sheath functioning to isolate the outer annulus of the casing and prevent formation fluid channeling, acts as an important barrier to the integrity of oil and gas wells. As the oil and gas exploration and development continuously extend to "deep, low, marine, and unconventional" resources, the proportion of oil and gas wells with complex geological conditions and complex down hole conditions increases year by year, the temperature and pressure conditions faced by the cement sheath are getting more and more complex, the demands on mechanical properties of set cement are increasing. In more and more wells, well-cementing designs not only require slurry property parameters such as density, thickening time, and stability of cement slurry, but also require mechanical property parameters such as compressive strength, Young's modulus, and Poisson's ratio of set cement. It is required to measure these parameters.

A compressive strength testing machine and cubic set cement specimens are mainly used in the related art, and uniaxial compressive strength of set cement is directly obtained; for other mechanical property parameters such as Young's modulus and Poisson's ratio, the test method is not explicitly specified, the conventional method is to use a uniaxial or triaxial mechanical testing machine, and a strain gauge is affixed to or an extensometer is used on a test specimen to carry out testing by uniaxial loading or unloading.

However, when using the above method for testing, to ensure accuracy of results, there are high requirements for the installation of the strain gauge or extensometer, and there are problems such as long test period, complex operation process, and high dependence on the experience of operators. In the meantime, the above method can only detect the deformation of a certain point or line on a specimen, and cannot fully reflect the whole deformation situation of the specimen, thereby causing a certain error in the result. In general, the existing test method has problems of long test period, complex operation process, high dependence on the experience of operators, and large error on measurement of Young's modulus and Poisson's ratio parameters of set cement specimens.

SUMMARY OF THE INVENTION

An object of the embodiments of the present disclosure is to provide a method and apparatus for measuring parameters of mechanical properties of set cement based on an image recognition technology, at least for solving the problems of long measurement period, complex operation process, and large measurement error on Young's modulus and Poisson's ratio of set cement specimens in the prior art.

In order to achieve the above object, the present disclosure provides, in one aspect, a method for measuring parameters of mechanical properties of set cement based on an image recognition technology, the method including:

- acquiring a first image of a set cement specimen, the first image being an image of the set cement specimen not subjected to a compressive load in a compressive test;
- extracting at least one feature point in the first image;
- acquiring a second image of the set cement specimen, the second image being an image of the set cement specimen subjected to a compressive load during the compressive test;
- determining a deformation gradient of the feature point by positions of the same feature point in the first image and the second image;
- determining a strain tensor by the deformation gradient; and
- determining a Young's modulus parameter and a Poisson's ratio parameter by the strain tensor.

In a second aspect, an apparatus for measuring parameters of mechanical properties of set cement based on an image recognition technology is provided, including:

- a first acquiring module, configured to acquire a first image of a set cement specimen, the first image being an image of the set cement specimen not subjected to a compressive load in a compressive test; an extracting module, configured to extract at least one feature point in the first image;
- a second acquiring module, configured to acquire a second image of the set cement specimen, the second image being an image of the set cement specimen subjected to a compressive load during the compressive test;
- a first determining module, configured to determine a deformation gradient of the feature point by positions of the same feature point in the first image and the second image;
- a second determining module, configured to determine a strain tensor by the deformation gradient; and
- a third determining module, configured to determine a Young's modulus parameter and a Poisson's ratio parameter by the strain tensor.

In a third aspect, an electronic device is provided, including:

- one or more processors; and
- a storage device, configured to store one or more programs;
- wherein the one or more programs, when executed by the one or more processors, cause the one or more processors to implement the method for measuring parameters of mechanical properties of set cement based on an image recognition technology in the embodiments.

In a fourth aspect, a computer-readable storage medium is provided, the computer-readable storage medium having a computer program stored thereon, which when executed by a processor, implements the method for measuring parameters of mechanical properties of set cement based on an image recognition technology in the embodiments.

Through the above technical solutions, the beneficial effects of the present disclosure are as follows:

- in the present disclosure, a first image and a second image of a set cement specimen are acquired, and a feature point in the first image is extracted, wherein the first image is an image of the set cement specimen not subjected to a compressive load in a compressive test, the second image is an image of the set cement specimen subjected to a compressive load during the compressive test, and the second image includes a feature point in the first image; then a deformation gradient of the feature point is determined by positions of the same feature point in the first image and the second image; a strain tensor is determined by the deformation gradient; and finally a Young's modulus parameter and a Poisson's ratio parameter are determined by the strain tensor. In this way, there is no need to install a strain gauge or an extensometer, rapid measurement of Young's modulus and Poisson's ratio of the set cement specimen can be realized; at the same time, the deformation situation of the plane or even the whole of the set cement specimen can be detected more rapidly, so that the measurement period of the Young's modulus and the Poisson's ratio of the set cement specimen can be shortened, the corresponding operation process is simplified, and the measurement error caused by a measurement operator or the like can be reduced due to the reduced participation of the measurement operator.

Other features and advantages of embodiments of the present disclosure will be described in detail in the detailed description section that follows.

BRIEF DESCRIPTION OF DRAWINGS

Accompanying drawings are included to provide a further understanding of embodiments of the present disclosure and constitute a part of this specification, and together with the detailed description below serve to explain, but not limit, embodiments of the present disclosure. In the drawings.

DESCRIPTION OF REFERENCE NUMERALS

1, pad;
2, set cement specimen;
3, platen;
4, compressive strength testing machine;
5, glass plate;
6, photographing apparatus;
7, compressive strength testing machine controller;
8, photographing controller; and
9, image collector.

DETAILED DESCRIPTION OF THE EMBODIMENTS

Unlike fluid parameter testing, when mechanical property testing is carried out, each test requires 3-5 set cement specimens to be measured for averaging due to the greater discretization of mechanical properties of cement-based materials, thus, there is a large demand for mechanical property testing of set cement during the design, research and development (R&D), and application of the well-cementing cement system. However, the measurement of Young's modulus and Poisson's ratio among the mechanical properties of set cement specimens requires that a strain gauge or extensometer is affixed to the set cement specimen as described in the Background section. Affixing the strain gauge or extensometer has high requirements and requires operators, therefore, the measurement of Young's modulus and Poisson's ratio parameters of the set cement specimens has problems of long test period, complex operation process, high dependence on the experience of operators, and large measurement error, and a method and apparatus for measuring parameters of mechanical properties of set cement based on an image recognition technology are specifically proposed in order to solve the above technical problems.

The specific implementation modes of the embodiments of the present disclosure are described in detail below in combination with the accompanying drawings. It should be understood that the specific implementation modes described herein are only used for describing and explaining the embodiments of the present disclosure and are not used for limiting the embodiments of the present disclosure.

Figure 1:
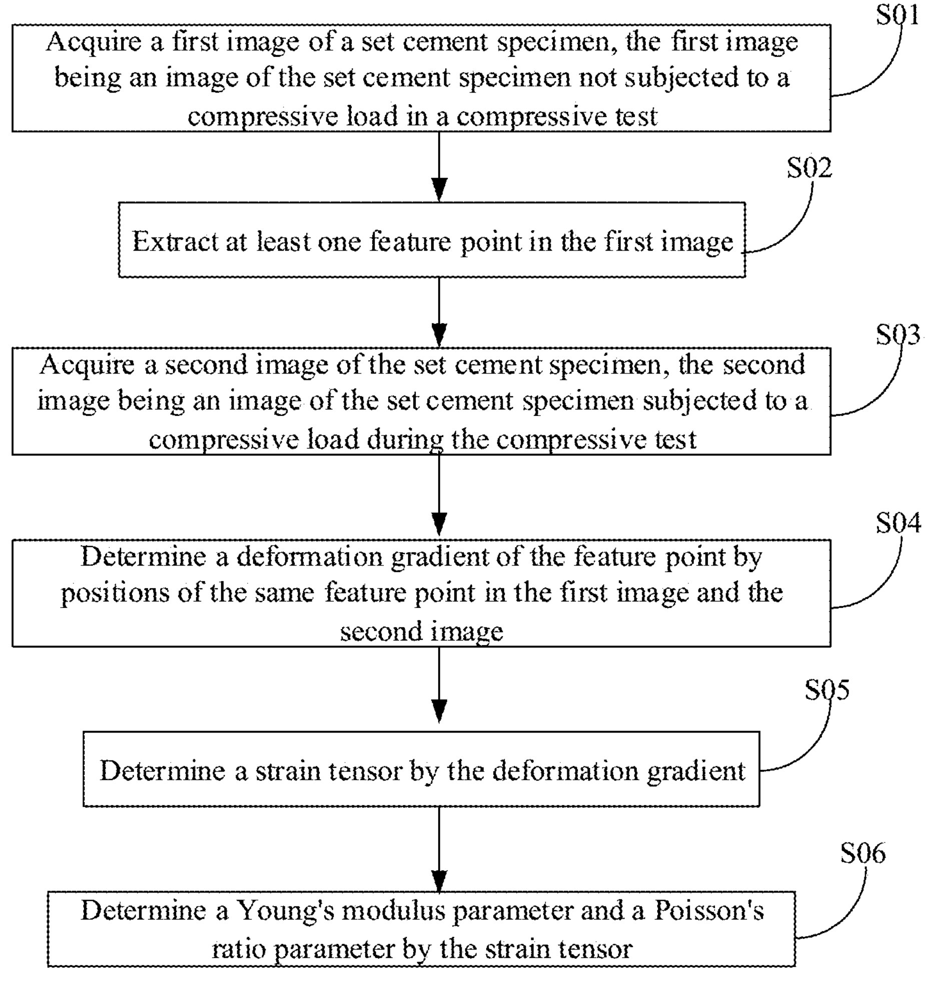
FIG. 1 is a flowchart of a method for measuring parameters of mechanical properties of set cement based on an image recognition technology provided by the present disclosure.

FIG. 1 is a flowchart of a method for measuring parameters of mechanical properties of set cement based on an image recognition technology provided by the present disclosure. As shown in FIG. 1, the present embodiment provides a method for measuring parameters of mechanical properties of set cement based on an image recognition technology, the method including:

S01: acquiring a first image of a set cement specimen, the first image being an image of the set cement specimen not subjected to a compressive load in a compressive test.

The first image may be acquired by a photographing apparatus in a detection device, and the specific structure of the detection device is introduced in detail in the following embodiments.

S02: extracting at least one feature point in the first image.

Feature points are readily recognizable points in the first image, and if the surface of the set cement specimen is smooth and homogeneous, the feature points can be artificially produced by randomly and uniformly spraying the surface of the set cement specimen with a matte paint that differs from the original color of the set cement specimen.

S03: acquiring a second image of the set cement specimen, the second image being an image of the set cement specimen subjected to a compressive load during the compressive test.

That is, the second image is an image taken when the set cement specimen is subjected to a compressive load during the test, when subjected to the compressive load, the set cement specimen will deform, and when the set cement specimen deforms, the feature point on its surface will also deform accordingly. The compressive load to which the set cement specimen is subjected refers to an axial compressive load in order to more easily measure the deformation of the set cement specimen.

S04: determining a deformation gradient of the feature point by positions of the same feature point in the first image and the second image.

In particular, the deformation gradient is determined by the following formula:

$$F_X = \frac{\partial X'}{\partial X}$$

where $F_X$ is the deformation gradient of the feature point, dimensionless; X is the coordinate of the feature point before deformation, in unit of mm; and X' is the coordinate of the feature point after deformation, in unit of mm, wherein the coordinate of the feature point can be obtained by the detection device.

S05: determining a strain tensor by the deformation gradient.

In particular, the strain tensor is determined by the following formula:

$$\varepsilon = \frac{1}{2}\left(F_X^T \times F_X - I\right)$$

where ε is the strain tensor, dimensionless; $F_X$ is the deformation gradient of the feature point, dimensionless;

$$F_x^T$$

is the transposed matrix of $F_X$, dimensionless; and I is an identity matrix, dimensionless.

S06: determining a Young's modulus parameter and a Poisson's ratio parameter by the strain tensor.

In particular, the Young's modulus parameter and the Poisson's ratio parameter are determined by the following formula:

calculating an axial stress to which the set cement specimen is subjected:

$$\sigma = \frac{F}{S};$$

calculating the Young's modulus parameter of the set cement specimen:

$$E = \frac{\sigma}{\varepsilon_{zz}};$$

calculating the Poisson's ratio parameter of the set cement specimen:

$$v = -\frac{\varepsilon_{zz}}{\varepsilon_H};$$

where σ is the axial stress to which the set cement specimen is subjected, in unit of MPa; F is an axial force to which the set cement specimen is subjected, in unit of N, and is obtained by the detection device; Sis the cross-sectional area of the set cement specimen, in unit of $mm^2$; E is the Young's modulus of the set cement specimen, in unit of GPa; $\varepsilon_{zs}$ is axial strain of the set cement specimen, determined by axial strain data in the strain tensor, dimensionless; v is the Poisson's ratio of the set cement specimen, dimensionless; and $\varepsilon_H$ is hoop strain of the set cement specimen, determined by radial strain data in the strain tensor, dimensionless.

In the present embodiment, the first image and the second image of the set cement specimen are acquired, and the feature point in the first image is extracted, wherein the first image is an image of the set cement specimen not subjected to a compressive load in a compressive test, the second image is an image of the set cement specimen subjected to a compressive load during the compressive test, and the second image includes a feature point in the first image; then a deformation gradient of the feature point is determined by positions of the same feature point in the first image and the second image; a strain tensor is determined by the deformation gradient; and finally a Young's modulus parameter and a Poisson's ratio parameter are determined by the strain tensor. In this way, there is no need to install a strain gauge or an extensometer, rapid measurement of Young's modulus and Poisson's ratio of the set cement specimen can be realized; at the same time, the deformation situation of the plane or even the whole of the set cement specimen can be detected more rapidly, so that the measurement period of the Young's modulus and the Poisson's ratio of the set cement specimen can be shortened, the corresponding operation process is simplified, and the measurement error caused by a measurement operator or the like can be reduced due to the reduced participation of the measurement operator.

Figure 2:
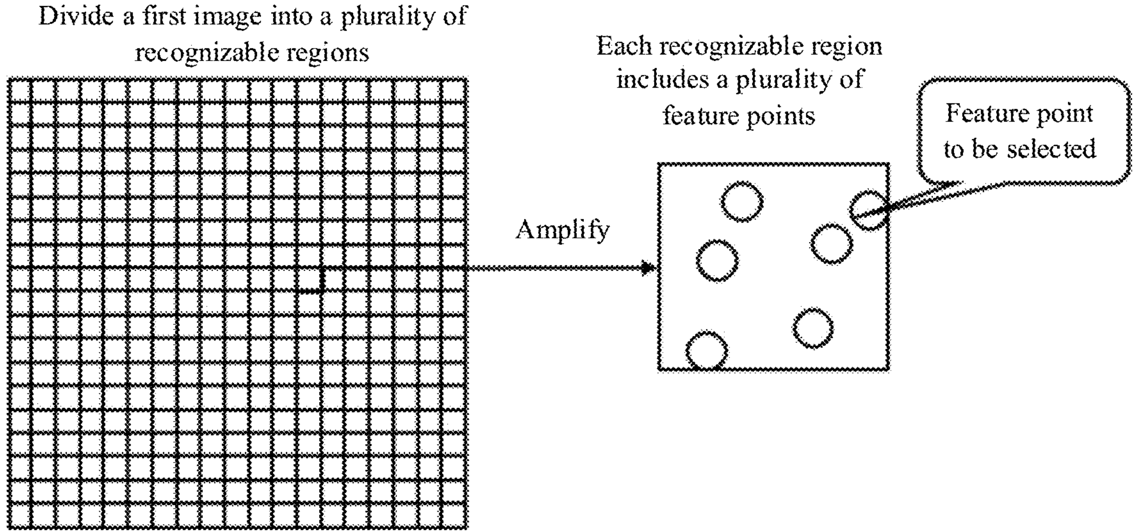
FIG. 2 is a schematic diagram of extracting a feature point in a first image in the method provided by the present disclosure.

In an embodiment, FIG. 2 is a schematic diagram of extracting a feature point in a first image in the method provided by the present disclosure. As shown in FIG. 2, after acquiring the first image of the set cement specimen, and before extracting at least one feature point in the first image, the method further includes:

extracting at least one recognizable region in the first image, each recognizable region comprising at least one feature point.

The number of first recognizable regions can be determined according to actual situation, when there is only one recognizable region, it represents that the entire first image acts as one first recognizable region, and the feature point can be more easily recognized by dividing the first recognizable region.

In an embodiment, to further facilitate recognizing the feature point, before extracting at least one recognizable region in the first image, the method further includes: grayscale scanning is performed on the first image. After performing grayscale scanning on the first image, it is more convenient to determine a series of feature points having the same gray value, so that it is more convenient to determine the coordinates of the feature points of the set cement specimen before deformation.

In an embodiment, to further facilitate recognizing the feature point in the second image, grayscale scanning can also be performed on the second image. After performing grayscale scanning on the second image, it is more convenient to determine a series of feature points having the same gray value after deformation, so that it is more convenient to determine the coordinates of the feature points of the set cement specimen after deformation.

Figure 3:
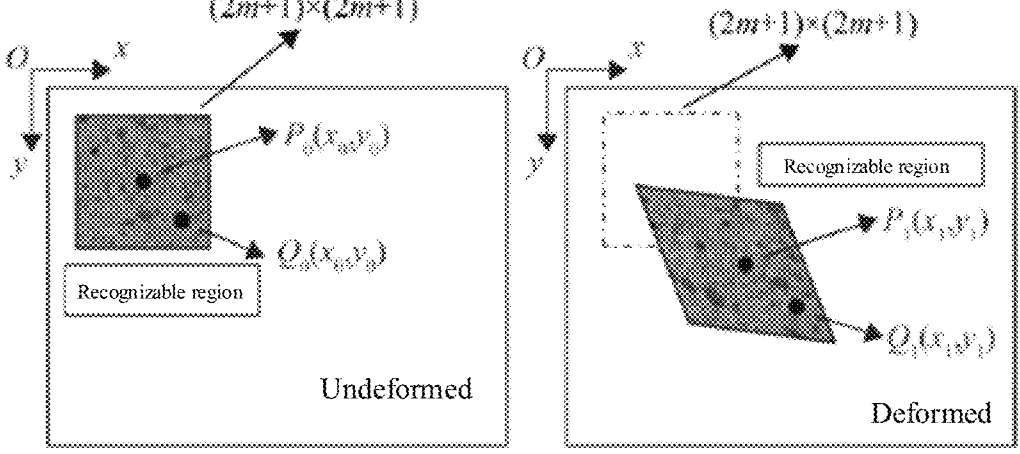
FIG. 3 is a schematic diagram illustrating feature points and feature point location tracking in the method provided by the present disclosure.

In an embodiment, FIG. 3 is a schematic diagram illustrating feature points and feature point location tracking in the method provided by the present disclosure. As shown in FIG. 3, before determining the deformation gradient of the feature point by positions of the same feature point in the first image and the second image, the method further includes:

establishing an image grayscale relationship of the same feature point in the first image and the second image.

The specific formula is as follows: $I(x,y,t)=I(x+u, y+v,t+\Delta t)$ where I represents a gray scale, in unit of %; x represents an x-axis coordinate of the feature point in the first image, in unit of mm; y is a y-axis coordinate of the feature point in the first image, in unit of mm; t is the photographing time of the first image, in unit of s; u is a variation amount of the x-axis coordinate of the feature point at a certain moment during the compressive test, in unit of mm; v is a variation amount of the y-axis coordinate of the feature point at a certain moment during the compressive test, in unit of mm; and $\Delta t$ is the time difference between the moment at which the second image is acquired and the moment at which the first image is acquired, in unit of s.

The image gray scale of the feature point can be obtained by grayscale scanning, and after establishing the image grayscale relationship of the same feature point in the first image and the second image, it is further more convenient to clearly and quickly acquire the coordinate positions of the feature point of the set cement specimen before and after deformation, thus making it more convenient to calculate the deformation gradient.

In an embodiment, the method further includes:

acquiring pressure data and time data of the set cement specimen subjected to the compressive load by the detection device, and calculating the compressive strength of the set cement specimen by the following formula:

$$\sigma 1 = \frac{F1}{S1}.$$

where σ1 is the compressive strength of the set cement specimen, in unit of MPa; F1 is the axial pressure when the set cement specimen is broken, in unit of N; and S1 is the cross-sectional area of the set cement specimen, in unit of $mm^2$.

The pressure data and the time data of the set cement specimen during compression can be continuously acquired by the detection device, so that the compressive strength parameter of the set cement specimen can be more easily obtained in combination with the corresponding image.

Figure 4:
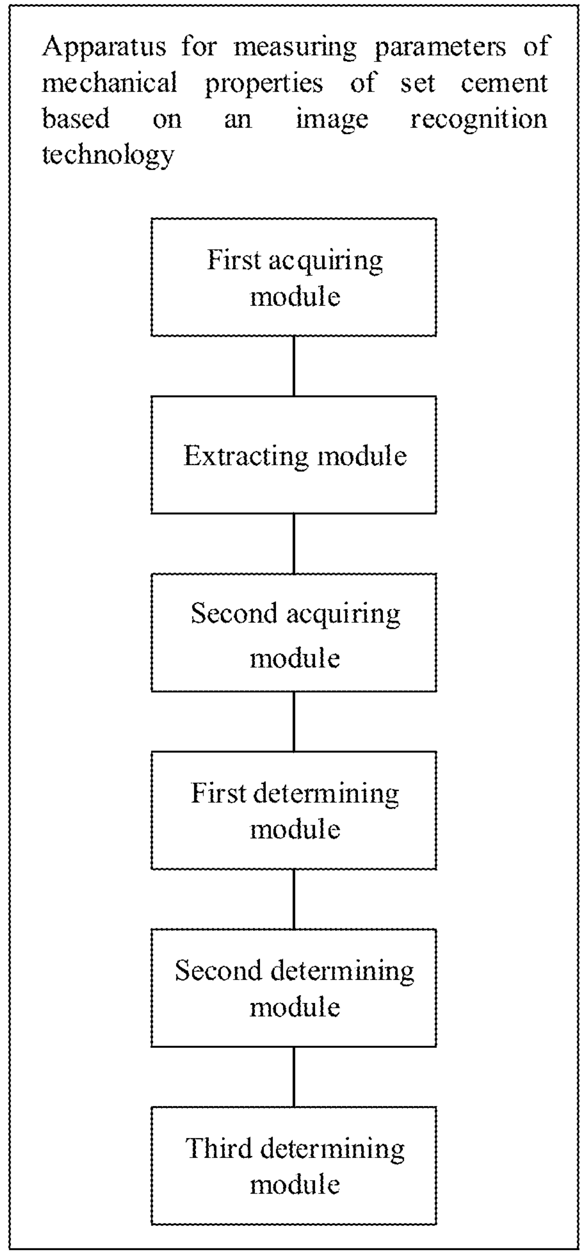
FIG. 4 is a schematic diagram of an apparatus for measuring parameters of mechanical properties of set cement based on an image recognition technology provided by the present disclosure.

FIG. 4 is a schematic diagram of an apparatus for measuring parameters of mechanical properties of set cement based on an image recognition technology provided by the present disclosure. As shown in FIG. 4, in an embodiment of the present disclosure, the present disclosure also provides an apparatus for measuring parameters of mechanical properties of set cement based on an image recognition technology, the apparatus including:

a first acquiring module, configured to acquire a first image of a set cement specimen, the first image being an image of the set cement specimen not subjected to a compressive load in a compressive test;

an extracting module, configured to extract at least one feature point in the first image;

a second acquiring module, configured to acquire a second image of the set cement specimen, the second image being an image of the set cement specimen subjected to a compressive load during the compressive test;

a first determining module, configured to determine a deformation gradient of the feature point by positions of the same feature point in the first image and the second image;

a second determining module, configured to determine a strain tensor by the deformation gradient; and a third determining module, configured to determine a Young's modulus parameter and a Poisson's ratio parameter by the strain tensor.

In the apparatus provided by the present embodiment, the first image and the second image of the set cement specimen are acquired, and the feature point in the first image is extracted, wherein the first image is an image of the set cement specimen not subjected to a compressive load in a compressive test, the second image is an image of the set cement specimen subjected to a compressive load during the compressive test, and the second image includes a feature point in the first image; then a deformation gradient of the feature point is determined by positions of the same feature point in the first image and the second image; a strain tensor is determined by the deformation gradient; and finally a Young's modulus parameter and a Poisson's ratio parameter are determined by the strain tensor. In this way, there is no need to install a strain gauge or an extensometer, rapid measurement of Young's modulus and Poisson's ratio of the set cement specimen can be realized; at the same time, the deformation situation of the plane or even the whole of the set cement specimen can be detected more rapidly, so that the measurement period of the Young's modulus and the Poisson's ratio of the set cement specimen can be shortened, the corresponding operation process is simplified, and the measurement error caused by a measurement operator or the like can be reduced due to the reduced participation of the measurement operator.

In an embodiment, the apparatus further includes: a first extracting module, configured to extract at least one recognizable region in the first image, each recognizable region including at least one feature point.

The number of first recognizable regions can be determined according to actual situation, when there is only one recognizable region, it represents that the entire first image acts as one first recognizable region, and the feature point can be more easily recognized by dividing the first recognizable region.

In an embodiment, to further facilitate recognizing the feature point, the apparatus further includes: a first scanning module, configured to perform grayscale scanning on the first image.

After performing grayscale scanning on the first image, it is more convenient to determine a series of feature points having the same gray value.

In an embodiment, to further facilitate recognizing the feature point, the apparatus further includes: a second scanning module, configured to perform grayscale scanning on the second image. After performing grayscale scanning on the second image, it is more convenient to determine a series of feature points having the same gray value after deformation, so that it is more convenient to determine the coordinates of the feature points before and after deformation.

Figure 5:
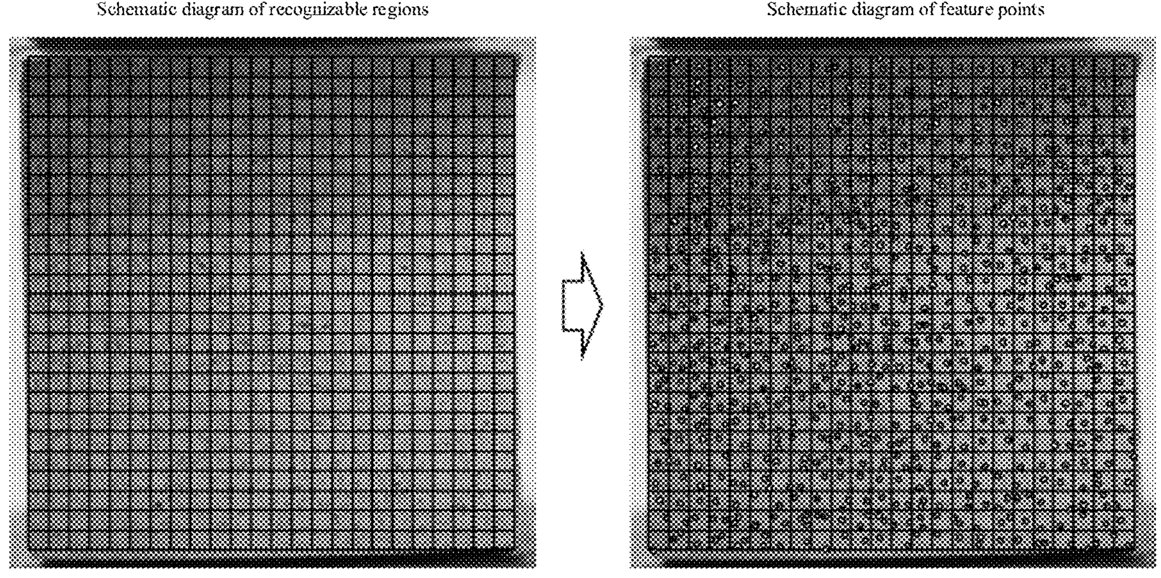
FIG. 5 is a structure diagram of a detection device in the apparatus provided by the present disclosure.

FIG. 5 is a schematic diagram of a detection device provided by the present disclosure, and the detection device is the same as the detection device in the method for measuring parameters of mechanical properties of set cement based on an image recognition technology, which is specifically described in this embodiment. As shown in FIG. 5, the detection device includes:

an experimental section, configured to apply a load to a set cement specimen, and collect and transmit a first image and a second image of the set cement specimen;

wherein the experimental section includes: a compressive strength testing machine 4, configured to apply a load to the set cement specimen 2; a platen 3, mounted on a loading shaft of the compressive strength testing machine 4 for transmitting a load of the compressive strength testing machine 4; and a photographing apparatus 6, mounted on the compressive strength testing machine 4 for taking the first image and the second image of the set cement specimen 2; and a data analysis processing section, configured to control a load applying action of the experimental section, and receive and process the first image and the second image;

wherein the data analysis processing section includes: a compressive strength testing machine controller 7, electrically connected to the compressive strength testing machine 4 for controlling load applying of the compressive strength testing machine 4 on the set cement specimen 2; a photographing controller 8, electrically connected to the photographing apparatus 6 for controlling a photographing action of the photographing apparatus 6 on the set cement specimen 2, and receiving the first image and the second image taken by the photographing apparatus 6; and an image collector 9, configured to receive and process the first image and the second image.

In the present embodiment, the set cement specimen 2 is placed in a corresponding position of the compressive strength testing machine 4, and the photographing apparatus 6 is controlled by the photographing controller 8 to take a first image, the photographing apparatus 6 herein may be a camera; then the compressive strength testing machine 4 is controlled to apply a load by the compressive strength testing machine controller 7; the loading shaft of the compressive strength testing machine 4 drives the platen 3 to move toward the set cement specimen 2 until the platen 3 generates an axial load on the set cement specimen 2; the compressive strength testing machine 4 continues to apply a load to the set cement specimen 2; and during this process, the photographing apparatus 6 installed on the compressive strength testing machine 4 is controlled by the photographing controller 8 to take a second image of the set cement specimen 2.

The photographing controller 8 transmits the first image and the second image taken by the photographing apparatus 6 to the image collector 9. The image collector integrates and a host of data analysis processing software of an image recognition technology, which is a host in the prior art. Then, corresponding processing is performed on the first image and the second image by the image collector 9. There are a plurality of second images, that is, the pressure value at each time point during the test and a second image of the set cement specimen can be collected in the above manner, and an image recognition technology is employed to process the corresponding image of the set cement specimen 2 to obtain the deformation situation of the set cement specimen 2, further to obtain the stress-strain curve of the set cement specimen 2, and finally to obtain the parameters of mechanical properties such as compressive strength, Young's modulus and Poisson's ratio of the set cement specimen 2 according to the above calculation method.

In an alternative embodiment, in order to allow a better placement of the set cement specimen on the compressive strength testing machine 4, the detection device also includes a pad 1, mounted on the compressive strength testing machine 4 and below the platen 3 for placing the set cement specimen 2. The axis of the pad 1 and the axis of the platen 3 are located on the same straight line, when the set cement specimen 2 is installed, the axis of the set cement specimen 2 and the axis of the pad 1 are also located on the same straight line, so that the axis of the set cement specimen 2 is located on the same straight line as the axis of the platen 3. Therefore, by using the pad 1, it can be more convenient to install the set cement specimen 2 on one hand, and on the other hand, it can be more convenient to position the set cement specimen 2, so that the load applied to the set cement specimen 2 by the platen 3 is applied to the center position of the set cement specimen 2, thus making the load of the set cement specimen 2 in the axial direction more uniform.

In an optional embodiment, a plurality of photographing apparatuses 6 are provided, and the plurality of photographing apparatuses 6 are evenly installed around the set cement specimen 2, that is the front, rear, left and right of the set cement specimen 2 can be provided with 1-4 photographing apparatuses 6, respectively. In this way, the plurality of photographing apparatuses 6 can photograph the set cement specimen 2 from different orientations at each time point, so that the first image and the second image can be obtained with more complete orientation and higher accuracy, and the parameters of mechanical properties such as compressive strength, Young's modulus and Poisson's ratio of the set cement specimen 2 can be obtained more accurately.

In an optional embodiment, in order to prevent that the set cement specimen is ruptured when loaded, and its debris damages the photographing apparatus 6, the detection device further includes a plurality of glass plates 5, the glass plates 5 are detachably mounted on the compressive strength testing machine 4 and between the set cement specimen 2 and the corresponding photographing apparatuses 6; the specific detachable mounting manner of the glass plate 5 can be achieved by conventional means; and four glass plates 5 can be provided and mounted in four directions of front, rear, left and right of the set cement specimen 2 for preventing the debris of the set cement specimen 2 after being ruptured from damaging the photographing apparatus 6.

In order to make the apparatus for measuring parameters of mechanical properties of set cement based on an image recognition technology clearer, it is explained below with reference to specific examples.

When the compressive strength, Young's modulus and Poisson's ratio parameters of set cement specimens are measured, the measurements are performed by the following steps:

Operation 1: a cured 50.8 mm×50.8 mm×50.8 mm cubical set cement specimen is ground flat on six sides and placed on the pad 1 of the compressive strength testing machine 4;

Operation 2: a plurality of photographing apparatuses 6 are fixed at the front, rear, left and right of the set cement specimen 2, and the photographing apparatuses 6 are ultra-high definition photographing apparatuses, so that the deformation situation of the set cement specimen 2 can be clearly photographed;

Operation 3: four detachable glass plates 5 are placed in front of the ultra-high definition photographing apparatuses at fixed positions, and distributed at the front, rear, left and right of the set cement specimen, which can protect the ultra-high definition photographing apparatuses from being damaged by scattering debris after the set cement specimen is broken;

Operation 4: the compressive strength testing machine 4 and the ultra-high definition photographing apparatuses are switched on, and the mechanical property test of the set cement specimen 2 begins;

Operation 5: the data analysis processing section collects and processes pressure, time, high-definition images and the like of the set cement specimens returned by the compressive strength testing machine and the four ultra-high definition photographing apparatuses in real time, and the compressive strength, the Young's modulus and the Poisson's ratio of the set cement are finally obtained through the image recognition technology; and Operation 6: at the end of the test, the broken set cement specimens 2 on the pad are cleared, and the compressive strength testing machine 4 and the ultra-high definition photographing apparatuses are switched off.

Figure 6:
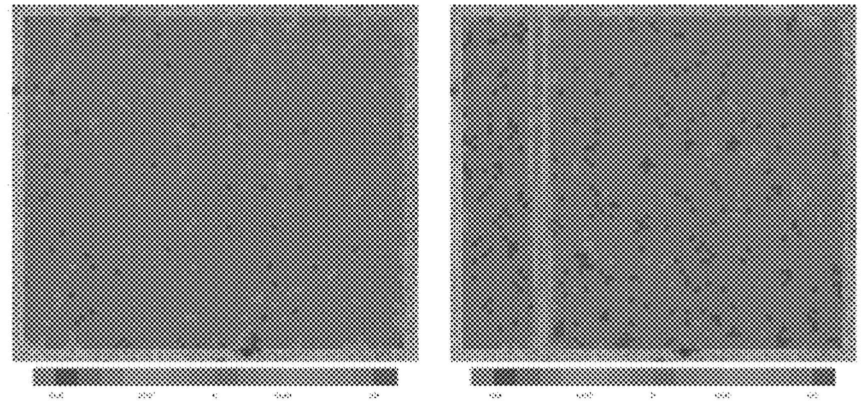
FIG. 6 is a schematic diagram illustrating recognizable regions and feature point determination in the apparatus provided by the present disclosure.
Figure 7:
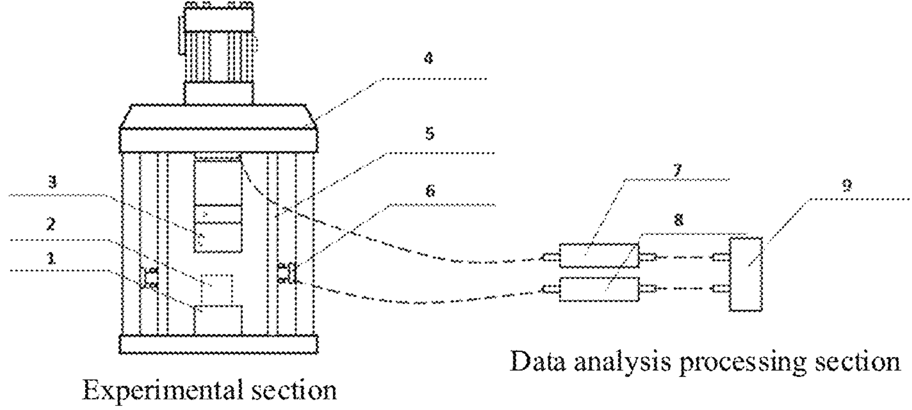
FIG. 7 is an analysis graph of a strain tensor of axial strain at two different pressure points in the apparatus provided by the present disclosure.

The image data analysis processing method is:

Step (1): pressure data, time data and the like of the pressing process of the set cement specimen 2 are obtained by the compressive strength testing machine;

Step (2): FIG. 6 is a schematic diagram illustrating recognizable regions and feature point determination in the apparatus provided by the present disclosure, as shown in FIG. 6, grayscale scanning is performed on the high-definition image of the set cement specimen 2 at an initial moment, recognizable regions are established, and feature points are determined;

Step (3): when the compressive strength test is carried out on the set cement specimen 2, the pressure increases every 1 N, the front, rear, left, and right of the set cement specimen 2 are simultaneously photographed until the set cement specimen is broken, then the test is ended;

Step (4): FIG. 7 is an analysis graph of a strain tensor of axial strain at two different pressure points in the apparatus provided by the present disclosure, and as shown in FIG. 7, images taken at different pressure points by the same photographing apparatus 6 are subjected to comparative analysis;

Step (5): assuming that the coordinate of a certain initial feature point of the high-definition image obtained by the photographing apparatus 6 in front of the set cement specimen 2 is X ($x_1$, $z_1$), the coordinate is X' ($\sqrt{0.2}x_1$, $\sqrt{1.8}z_1$) when the pressure reaches 10 N, a deformation gradient can be obtained by the formula $$F_X = \frac{\partial X'}{\partial X} = \begin{bmatrix} \sqrt{0.2} & 0 \\ 0 & \sqrt{1.8} \end{bmatrix},$$

and further a strain tensor in front of the set cement specimen 2 under the condition that the pressure varies to 10 N is obtained by the formula $$\varepsilon = \begin{bmatrix} \varepsilon_{xx} & \varepsilon_{xz} \\ \varepsilon_{zx} & \varepsilon_{zz} \end{bmatrix} = \frac{1}{2}(F^T \times F - I) = \frac{1}{2}\left(\begin{bmatrix} \sqrt{0.2}, 0 \\ 0, \sqrt{1.8} \end{bmatrix} \times \begin{bmatrix} \sqrt{0.2}, 0 \\ 0, \sqrt{1.8} \end{bmatrix} - \begin{bmatrix} 1, 0 \\ 0, 1 \end{bmatrix}\right) = \begin{bmatrix} -0.4 & 0 \\ 0 & 0.4 \end{bmatrix};$$

Step (6): the high-definition images obtained by the photographing apparatuses 6 at the rear, left and right of the set cement specimen 2 are analyzed similarly, and the strain tensors under the condition that the pressure varies to 10 N are obtained, which is shown as follows:

$$\varepsilon 1 = \begin{bmatrix} \varepsilon_{xx} & \varepsilon_{xz} \\ \varepsilon_{zx} & \varepsilon_{zz} \end{bmatrix} = \frac{1}{2}(F^T \times F - I) = \frac{1}{2}\left(\begin{bmatrix} \sqrt{0.2}, 0 \\ 0, \sqrt{2} \end{bmatrix} \times \begin{bmatrix} \sqrt{0.2}, 0 \\ 0, \sqrt{2} \end{bmatrix} - \begin{bmatrix} 1, 0 \\ 0, 1 \end{bmatrix}\right) = \begin{bmatrix} -0.4 & 0 \\ 0 & 0.5 \end{bmatrix}$$

$$\varepsilon 2 = \begin{bmatrix} \varepsilon_{xx} & \varepsilon_{xz} \\ \varepsilon_{zx} & \varepsilon_{zz} \end{bmatrix} = \frac{1}{2}(F^T \times F - I) = \frac{1}{2}\left(\begin{bmatrix} \sqrt{0.4}, 0 \\ 0, \sqrt{1.8} \end{bmatrix} \times \begin{bmatrix} \sqrt{0.4}, 0 \\ 0, \sqrt{1.8} \end{bmatrix} - \begin{bmatrix} 1, 0 \\ 0, 1 \end{bmatrix}\right) = \begin{bmatrix} -0.3 & 0 \\ 0 & 0.4 \end{bmatrix}$$

$$\varepsilon 3 = \begin{bmatrix} \varepsilon_{xx} & \varepsilon_{xz} \\ \varepsilon_{zx} & \varepsilon_{zz} \end{bmatrix} = \frac{1}{2}(F^T \times F - I) = \frac{1}{2}\left(\begin{bmatrix} \sqrt{0.6}, 0 \\ 0, \sqrt{1.6} \end{bmatrix} \times \begin{bmatrix} \sqrt{0.6}, 0 \\ 0, \sqrt{1.6} \end{bmatrix} - \begin{bmatrix} 1, 0 \\ 0, 1 \end{bmatrix}\right) = \begin{bmatrix} -0.2 & 0 \\ 0 & 0.3 \end{bmatrix};$$

Step (7): calculation is performed at each pressure point according to the processes of step (4)-step (6), thereby plotting a stress-strain $\varepsilon_{zz}$ (i.e., stress-axial strain) curve and a strain $\varepsilon_{zz}$-strain $\varepsilon_H$ (i.e., axial strain-hoop strain) curve of the set cement specimen;

Step (8): the Young's modulus of the set cement specimen is calculated by combining the formula $$\sigma = \frac{F}{S}$$

and the formula $$E = \frac{\sigma}{\varepsilon_{ZZ}}$$

and taking the pressure reaching 10 N as an example, which is shown in the following formula:

$$E = \frac{F}{S \times \overline{\varepsilon}_{zz}} = \frac{10}{50.8 \times 50.8 \times \frac{(0.4 + 0.5 + 0.4 + 0.3)}{4}} = 9.69 GPa;$$

and

Step (9): the Poisson's ratio of the set cement specimen 2 is calculated according to the formula $$v = -\frac{\varepsilon_{ZZ}}{\varepsilon_H}$$

and by taking the pressure reaching 10 N as an example, which is shown in the following formula:

$$v = -\frac{\overline{\varepsilon}_{zz}}{\varepsilon_H} = \frac{\frac{(0.4 + 0.5 + 0.4 + 0.3)}{4}}{-(0.4 + 0.4 + 0.3 + 0.2)} = 0.31.$$

The specific definition of the apparatus for measuring parameters of mechanical properties of set cement based on an image recognition technology can be referred to the above definition of the method for measuring parameters of mechanical properties of set cement based on an image recognition technology, which is not repeated herein. Various modules in the above apparatus may be implemented in whole or in part by software, hardware, and a combination thereof. Each of the above modules may be embedded in a processor in a computer device in the form of hardware or may separate from a processor in a computer device, or may be stored in a memory in the computer device in the form of software, so that the processor calls to perform the operations corresponding to each of the above modules.

Figure 8:
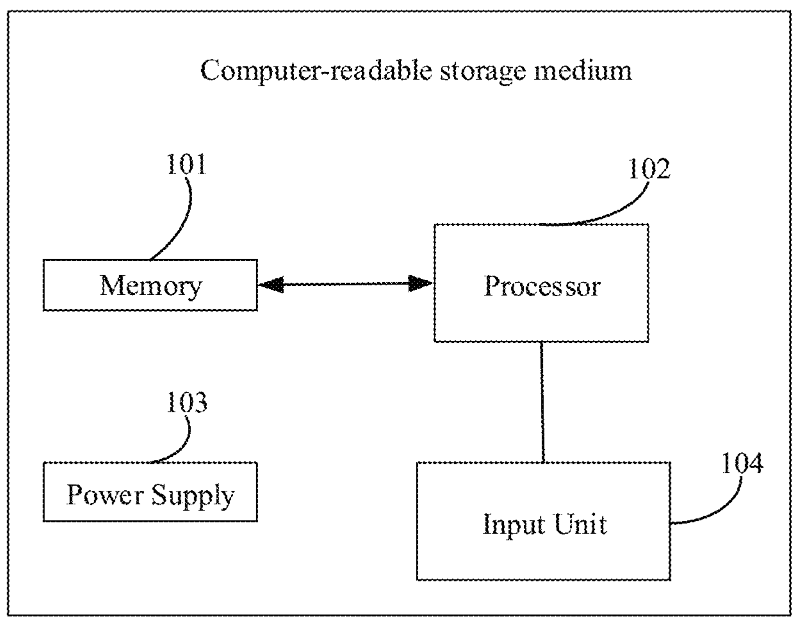
FIG. 8 is a structure diagram of an electronic device in the method provided by the present disclosure.

In another alternative implementation, FIG. 8 is a structure diagram of an electronic device in the method provided by the present disclosure. As shown in FIG. 8, the present embodiment discloses an electronic device, and a structure diagram of an electronic device according to an embodiment of the present disclosure is specifically shown:

the electronic device includes components such as a memory 101, one or more processors 102, a power supply 103 and an input unit 104. It will be appreciated by those skilled in the art that the configuration of the electronic device shown in FIG. 8 does not constitute a limitation of the electronic device, and may include more or fewer components than those shown, or a combination of certain components, or a different arrangement of components.

The processor 102 is a control center of the electronic device, using various interfaces and lines to connect various parts of the whole electronic device, performing various functions of the electronic device, and processing data by running or executing software programs and/or modules stored in the memory 101, and invoking data stored in the memory 101, thereby monitoring the electronic device as a whole. Optionally, the processor 102 may include one or more processing cores; preferably, the processor 102 integrates an application processor and a modem processor, wherein the application processor mainly processes an operating system, a user interface, an application program, and the like, and the modem processor mainly processes wireless communication. It will be appreciated that the above modem processor may not be integrated into the processor 102.

The memory 101 may be used to store software programs and modules, and the processor 102 executes various functional applications and data processing by running the software programs and modules stored in the memory 101. The memory 101 may mainly include a stored program area and a stored data area, wherein the stored program area may store an operating system, an application program required for at least one function (such as a sound playing function, and an image playing function), and the like; the stored data area may store data created according to the use of the electronic device, and the like. In addition, the memory 101 may include a high-speed random access memory, and may further include a non-volatile memory, for example, at least one magnetic disk storage device, flash memory device, or other volatile solid-state memory device. Accordingly, the memory 101 may further include a memory controller to provide access to the memory 101 by the processor 102.

The electronic device further includes a power supply 103 for supplying power to various components. Preferably, the power supply 103 may be logically coupled to the processor 102 through a power management system to manage charging, discharging, and power consumption management through the power management system. The power supply 103 may further include any of one or more of a DC or AC power supply, a recharging system, a power failure detection circuit, a power converter or inverter, a power status indicator, and the like.

The electronic device may further include an input unit 104 that may be used to receive entered numeric or character information, and to generate keyboard, mouse, joystick, optical, or trackball signal inputs related to user settings and function control.

In spite of not showing, the electronic device may further include a display unit and the like, which will not be repeated herein. Specifically, in the present embodiment, the one or more programs in the electronic device, when executed by the one or more processors 102, cause the one or more processors 102 to implement the method for measuring parameters of mechanical properties of set cement based on an image recognition technology in the above embodiments.

It will be understood by those of ordinary skill in the art that all or a portion of steps in various methods of the above embodiments may be performed via instructions that may be stored in a computer-readable storage medium and loaded and executed by a processor, or via associated hardware controlled by instructions.

In another embodiment, a computer-readable storage medium is also provided, the computer-readable storage medium having a computer program stored thereon, which when executed by a processor, implements the method for measuring parameters of mechanical properties of set cement based on an image recognition technology in the above embodiments.

It will be understood by those of ordinary skill in the art that embodiments of the present disclosure may be provided as a method, apparatus, or computer program product. Accordingly, the present disclosure may take the form of an exclusive hardware embodiment, an exclusive software embodiment or an embodiment combining software and hardware aspects. Furthermore, the present disclosure may take the form of a computer program product implemented on one or more computer usable storage media (including but not limited to disk storage, CD-ROM, optical storage, etc.) having computer usable program codes therein.

The present disclosure is described with reference to flowcharts and/or block diagrams of methods, apparatuses, and computer program products according to embodiments of the present disclosure. It should be understood that each flow and/or each block in the flowcharts and/or block diagrams, and combinations of flows and/or blocks in the flowcharts and/or block diagrams can be implemented by computer program instructions. These computer program instructions may be provided to a processor of a general purpose computer, a special purpose computer, an embedded processor, or other programmable data processing device to produce a machine, so that instructions, which are executed by the processor of the computer or other programmable data processing device, are caused to produce means for implementing the functions specified in one flow or more flows of the flowcharts and/or one block or more blocks of the block diagrams.

These computer program instructions may also be stored in a computer-readable memory that can direct a computer or other programmable data processing device to function in a particular manner, so that instructions stored in the computer-readable memory are caused to produce an article of manufacture including instruction means which implements the functions specified in one flow or more flows of the flowcharts and/or one block or more blocks of the block diagrams.

These computer program instructions may also be loaded onto a computer or other programmable data processing device, and a series of operation steps are caused to be performed on the computer or other programmable device to produce a computer-implemented process such that instructions, which are executed on the computer or other programmable device, provide steps for implementing the functions specified in one flow or more flows of the flowcharts and/or one block or more blocks of the block diagrams.

Finally, it should be noted that the above embodiments are only used to illustrate, but not limit the technical solutions of the present disclosure, although the present disclosure has been described in detail with reference to the above embodiments, it will be understood by those skilled in the art that modifications or equivalents may be made to the specific implementation modes of the present disclosure without departing from the spirit and scope of the present disclosure as defined by the appended claims.

The invention claimed is:

1. A method for measuring set cement mechanical properties based on an image recognition technology, comprising:

acquiring a first image of a set cement specimen taken by a photographing apparatus, the first image being an image of the set cement specimen not subjected to a compressive load in a compressive test;

extracting at least one feature point in the first image;

acquiring a second image of the set cement specimen taken by the photographing apparatus, the second image being an image of the set cement specimen subjected to a compressive load during the compressive test;

performing grayscale scanning on the first image and the second image, establishing an image grayscale relationship of the same feature point in the first image and the second image, acquiring the positions of the feature point based on the image grayscale relationship, and determining a deformation gradient of the feature point by positions of the same feature point in the first image and the second image;

determining a strain tensor by the deformation gradient; and determining a Young's modulus parameter and a Poisson's ratio parameter by the strain tensor, wherein, the image grayscale relationship is configured as:

$$I(x, y, t) = I(x+u, y+v, t+\Delta t)$$

wherein I represents a gray scale, in unit of %; x represents an x-axis coordinate of the feature point in the first image, in unit of mm; y is a y-axis coordinate of the feature point in the first image, in unit of mm; t is the photographing time of the first image, in unit of s; u is a variation amount of the x-axis coordinate of the feature point at a certain moment during the compressive test, in unit of mm; v is a variation amount of the y-axis coordinate of the feature point at a certain moment during the compressive test, in unit of mm; and $\Delta t$ is the time difference between the moment at which the second image is acquired and the moment at which the first image is acquired, in unit of s.

2. The method according to claim 1, wherein after acquiring the first image of the set cement specimen, and before extracting the at least one feature point in the first image, the method further comprises:

extracting at least one recognizable region in the first image, each recognizable region comprising at least one feature point.

3. The method according to claim 1, wherein determining the deformation gradient of the feature point by the positions of the same feature point in the first image and the second image comprises:

$$F_X = \frac{\partial X'}{\partial X}$$

wherein $F_X$ is the deformation gradient of the feature point, dimensionless; X is the coordinate of the feature point before deformation, in unit of mm; and X' is the coordinate of the feature point after deformation, in unit of mm.

4. The method according to claim 3, wherein determining the strain tensor by the deformation gradient, comprises:

$$\varepsilon = \frac{1}{2}\left(F_X^T \times F_X - I\right)$$

wherein ε is the strain tensor, dimensionless; $F_X$ is the deformation gradient of the feature point, dimensionless;

$$F_x^T$$

is the transposed matrix of $F_X$, dimensionless; and I is an identity matrix, dimensionless.

5. The method according to claim 4, wherein determining the Young's modulus parameter and the Poisson's ratio parameter by the strain tensor comprises:

calculating an axial stress to which the set cement specimen is subjected:

$$\sigma = \frac{F}{S};$$

calculating the Young's modulus parameter of the set cement specimen:

$$E = \frac{\sigma}{\varepsilon_{zz}}; \text{ and}$$

calculating the Poisson's ratio parameter of the set cement specimen:

$$v = -\frac{\varepsilon_{zz}}{\varepsilon_H};$$

wherein σ is the axial stress to which the set cement specimen is subjected, in unit of MPa; Fis an axial force to which the set cement specimen is subjected, in unit of N, and is obtained by a detection device; S is the cross-sectional area of the set cement specimen, in unit of $mm^2$; E is the Young's modulus of the set cement specimen, in unit of GPa; $\varepsilon_{zz}$ is axial strain of the set cement specimen, determined by axial strain data in the strain tensor, dimensionless; ν is the Poisson's ratio of the set cement specimen, dimensionless; and $\varepsilon_H$ is hoop strain of the set cement specimen, determined by radial strain data in the strain tensor, dimensionless.

6. The method according to claim 1, wherein the method further comprises:

acquiring pressure data and time data of the set cement specimen subjected to the compressive load by the detection device, and calculating the compressive strength of the set cement specimen by the following formula:

$$\sigma 1 = \frac{F1}{S1}$$

wherein σ1 is the compressive strength of the set cement specimen, in unit of MPa; F1 is the axial pressure when the set cement specimen is broken, in unit of N; and S1 is the cross-sectional area of the set cement specimen, in unit of $mm^2$.

7. An apparatus for measuring set cement mechanical properties based on an image recognition technology, wherein the apparatus comprises a detection device, and detection device comprising:

an experimental section, configured to acquire a first image and a second image of a set cement specimen, the first image being an image of the set cement specimen not subjected to a compressive load in a compressive test, the second image being an image of the set cement specimen subjected to a compressive load during the compressive test;

a data analysis processing section, configured to:

extract at least one feature point in the first image;

perform grayscale scanning on the first image and the second image;

establish an image grayscale relationship of the same feature point in the first image and the second image;

acquire the positions of the feature point based on the image grayscale relationship;

determine a deformation gradient of the feature point by positions of the same feature point in the first image and the second image;

determine a strain tensor by the deformation gradient; and determine a Young's modulus parameter and a Poisson's ratio parameter by the strain tensor, wherein, the image grayscale relationship is configured as:

$$I(x, y, t) = I(x + u, y + v, t + \Delta t)$$

wherein I represents a gray scale, in unit of %; x represents an x-axis coordinate of the feature point in the first image, in unit of mm; y is a y-axis coordinate of the feature point in the first image, in unit of mm; t is the photographing time of the first image, in unit of s; u is a variation amount of the x-axis coordinate of the feature point at a certain moment during the compressive test, in unit of mm; v is a variation amount of the y-axis coordinate of the feature point at a certain moment during the compressive test, in unit of mm; and Δt is the time difference between the moment at which the second image is acquired and the moment at which the first image is acquired, in unit of s.

8. The apparatus according to claim 7, wherein the experimental section comprises:

a compressive strength testing machine (4), configured to apply a load to the set cement specimen (2);

a platen (3), mounted on a loading shaft of the compressive strength testing machine (4) for transmitting a load of the compressive strength testing machine (4); and a photographing apparatus (6), mounted on the compressive strength testing machine (4) for taking the first image and the second image of the set cement specimen (2).

9. The apparatus according to claim 8, wherein the data analysis processing section comprises:

a compressive strength testing machine controller (7), electrically connected to the compressive strength testing machine (4) for controlling load applying of the compressive strength testing machine (4) on the set cement specimen (2);

a photographing controller (8), electrically connected to the photographing apparatus (6) for controlling a photographing action of the photographing apparatus (6) on the set cement specimen (2), and receiving the first image and the second image taken by the photographing apparatus (6); and an image collector (9), configured to receive and process the first image and the second image.

10. The apparatus according to claim 8, wherein the experimental section further comprises:

a pad (1), mounted on the compressive strength testing machine (4) and below the platen (3) for placing the set cement specimen (2).

11. The apparatus according to claim 8, wherein a plurality of photographing apparatuses (6) are provided, and the plurality of photographing apparatuses (6) are evenly installed around the set cement specimen (2).

12. The apparatus according to claim 11, wherein the experimental section further comprises:

a plurality of glass plates (5), detachably mounted on the compressive strength testing machine (4) and between the set cement specimen (2) and the corresponding photographing apparatuses (6).

13. An electronic device, comprising:

one or more processors;

a storage device, configured to store one or more programs;

wherein the one or more programs, when executed by the one or more processors, cause the one or more processors to implement a method for measuring set cement mechanical properties based on an image recognition technology, wherein the method comprises:

acquiring a first image of a set cement specimen taken by a photographing apparatus, the first image being an image of the set cement specimen not subjected to a compressive load in a compressive test;

extracting at least one feature point in the first image;

acquiring a second image of the set cement specimen taken by the photographing apparatus, the second image being an image of the set cement specimen subjected to a compressive load during the compressive test;

performing grayscale scanning on the first image and the second image, establishing an image grayscale relationship of the same feature point in the first image and the second image, acquiring the positions of the feature point based on the image grayscale relationship, and determining a deformation gradient of the feature point by positions of the same feature point in the first image and the second image;

determining a strain tensor by the deformation gradient; and determining a Young's modulus parameter and a Poisson's ratio parameter by the strain tensor, wherein, the image grayscale relationship is configured as:

$$I(x, y, t) = I(x+u, y+v, t+\Delta t)$$

wherein I represents a gray scale, in unit of %; x represents an x-axis coordinate of the feature point in the first image, in unit of mm; y is a y-axis coordinate of the feature point in the first image, in unit of mm; tis the photographing time of the first image, in unit of s; u is a variation amount of the x-axis coordinate of the feature point at a certain moment during the compressive test, in unit of mm; v is a variation amount of the y-axis coordinate of the feature point at a certain moment during the compressive test, in unit of mm; and $\Delta t$ is the time difference between the moment at which the second image is acquired and the moment at which the first image is acquired, in unit of s.

14. The electronic device according to claim 13, wherein after acquiring the first image of the set cement specimen, and before extracting the at least one feature point in the first image, the method further comprises:

extracting at least one recognizable region in the first image, each recognizable region comprising at least one feature point.

15. The electronic device according to claim 13, wherein determining the deformation gradient of the feature point by the positions of the same feature point in the first image and the second image comprises:

$$F_X = \frac{\partial X'}{\partial X}$$

wherein $F_X$ is the deformation gradient of the feature point, dimensionless; X is the coordinate of the feature point before deformation, in unit of mm; and X' is the coordinate of the feature point after deformation, in unit of mm.

16. The electronic device according to claim 15, wherein determining the strain tensor by the deformation gradient, comprises:

$$\varepsilon = \frac{1}{2}\left(F_X^T \times F_X - I\right)$$

wherein $\varepsilon$ is the strain tensor, dimensionless; $F_X$ is the deformation gradient of the feature point, dimensionless;

$$F_x^T$$

is the transposed matrix of $F_X$, dimensionless; and I is an identity matrix, dimensionless.

17. The electronic device according to claim 16, wherein determining the Young's modulus parameter and the Poisson's ratio parameter by the strain tensor comprises:

calculating an axial stress to which the set cement specimen is subjected:

$$\sigma = \frac{F}{S};$$

calculating the Young's modulus parameter of the set cement specimen:

$$E = \frac{\sigma}{\varepsilon_{zz}}; \text{ and}$$

calculating the Poisson's ratio parameter of the set cement specimen:

$$v = -\frac{\varepsilon_{zz}}{\varepsilon_H};$$

wherein $\sigma$ is the axial stress to which the set cement specimen is subjected, in unit of MPa; Fis an axial force to which the set cement specimen is subjected, in unit of N, and is obtained by a detection device; S is the cross-sectional area of the set cement specimen, in unit of $mm^2$; E is the Young's modulus of the set cement specimen, in unit of GPa; $\varepsilon_{zz}$ is axial strain of the set cement specimen, determined by axial strain data in the strain tensor, dimensionless; $\nu$ is the Poisson's ratio of the set cement specimen, dimensionless; and $\varepsilon_H$ is hoop strain of the set cement specimen, determined by radial strain data in the strain tensor, dimensionless.

18. The electronic device according to claim 13, wherein the method further comprises:

acquiring pressure data and time data of the set cement specimen subjected to the compressive load by the detection device, and calculating the compressive strength of the set cement specimen by the following formula:

$$\sigma 1 = \frac{F1}{S1}$$

wherein σ1 is the compressive strength of the set cement specimen, in unit of MPa; F1 is the axial pressure when the set cement specimen is broken, in unit of N; and S1 is the cross-sectional area of the set cement specimen, in unit of $mm^2$.

* * * * *